United States Patent
Abd El-Lateef Ahmed et al.

(10) Patent No.: US 11,730,759 B1
(45) Date of Patent: Aug. 22, 2023

(54) SULFASALAZINE-LOADED ZINC OXIDE NANOPARTICLES FOR THE TREATMENT OF ULCERATIVE COLITIS

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Ahmed Mohammed Abu-Dief Mohammed, Al-Ahsa (SA); Mohammed Sherif Saddik Ibrahim, Al-Ahsa (SA); Ali Khames Abd Eltwab Morsy, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/119,526

(22) Filed: Mar. 9, 2023

(51) Int. Cl.
*A61K 33/30* (2006.01)
*A61K 9/14* (2006.01)
*A61P 1/04* (2006.01)
*A61K 31/635* (2006.01)

(52) U.S. Cl.
CPC ............. *A61K 33/30* (2013.01); *A61K 9/145* (2013.01); *A61K 31/635* (2013.01); *A61P 1/04* (2018.01)

(58) Field of Classification Search
CPC ...... A61K 9/145; A61K 31/635; A61K 33/30; A61P 1/04
See application file for complete search history.

(56) References Cited

U.S. PATENT DOCUMENTS

| | | |
|---|---|---|
| 2013/0295012 A1 | 11/2013 | Ingber et al. |
| 2015/0290092 A1 | 10/2015 | Shieh |
| 2018/0280536 A1 | 10/2018 | Sicard et al. |
| 2019/0091350 A1 | 3/2019 | Peyman |
| 2020/0246179 A1 | 8/2020 | Peyman |
| 2021/0052533 A1 | 2/2021 | Cox et al. |
| 2021/0138066 A1 | 5/2021 | Abundo et al. |

OTHER PUBLICATIONS

Miasuda, et al.; "Comparison of the effect of mesalazine and sulfasalazine on laboratory parameters: a retrospective observational study."; European Journal of Clinical Pharmacology; 2012.
Abdolahi, et al.; "Gold decorated B N nanocluster as an effective sulfasalazine drug carrier: A theoretical investigation."; Physica E: Low-dimensional Systems and Nanostructures; vol. 124, Oct. 2020.
Kumar, et al.; "Investigation of Adsorption Behavior of Anticancer Drug on Zinc Oxide Nanoparticles: A Solid State NMR and Cyclic Voltammetry (CV) Analysis."; J Pharm Sci; Nov. 2021.
Li, et al.; "ZnO nanoparticles act as supportive therapy in DSS-induced ulcerative colitis in mice by maintaining gut homeostasis and activating Nrf2 signaling."; Scientific Reports, 2017.
Khodir, et al.; "Targeting Nrf2/HO-1 signaling by crocin: Role in attenuation of AA-induced ulcerative colitis in rats."; Biomedicine & Pharmacotherapy vol. 110, Feb. 2019, pp. 389-399.
El-Maddawy, et al.; "Use of Zinc Oxide Nanoparticles as Anticoccidial Agents in Broiler Chickens along with Its Impact on Growth Performance, Antioxidant Status, and Hematobiochemical Profile "; Life (Basel), Jan. 5, 2022.

*Primary Examiner* — Ali Soroush
(74) *Attorney, Agent, or Firm* — Nath, Goldberg & Meyer; Richard C. Litman

(57) ABSTRACT

A composition for treating ulcerative colitis can include zinc oxide nanoparticles; and sulfasalazine adsorbed onto a surface of the zinc oxide nanoparticles. The composition can be administered to a patient to treat ulcerative colitis or symptoms associated with ulcerative colitis. The composition can be administered at about 100 mg/kg of zinc oxide nanoparticles and up to about 12.2 mg/kg of sulfasalazine. These compositions exhibit synergistic effects in treating ulcerative colitis.

11 Claims, No Drawings

SULFASALAZINE-LOADED ZINC OXIDE NANOPARTICLES FOR THE TREATMENT OF ULCERATIVE COLITIS

BACKGROUND

1. Field

The disclosure of the present patent application relates to a composition for the treatment of ulcerative colitis and, particularly, to a composition including sulfasalazine loaded zinc oxide nanoparticles (ZnONPs).

2. Description of the Related Art

Irritable Bowel Syndrome (IBS) is part of a spectrum of diseases known as functional gastrointestinal disorders which include diseases such as non-cardiac chest pain, non-ulcer dyspepsia, and chronic constipation or diarrhea. These diseases are all characterized by chronic or recurrent gastrointestinal symptoms for which no structural or biochemical cause can be found. Patients suffering from IBD and IBS share several kinds of symptoms.

Ulcerative colitis (UC) and Crohn's Disease (CD) are inflammatory bowel diseases (IBD) characterized by chronic inflammation in the intestines, UC occurs in the colon while CD may be present in the entire gastrointestinal (GI) tract. The clinical symptoms are diarrhea, abdominal pain, occasional rectal bleeding, weight loss, tiredness and sometimes fever. Although occurring at any age, IBD is most common in teenagers and young adults, which consequently may suffer from delayed development and stunted growth.

Ulcerative colitis is typically treated medically by reducing the inflammation and thereby controlling the gastrointestinal symptoms. However, a medical cure for ulcerative colitis has not yet been disclosed.

A current standard treatment for ulcerative colitis is sulfasalazine. However, upon administration to a patient, sulfasalazine can be metabolically converted into 5-amino salicylic acid (5-ASA) and sulfapyridine, reducing its absorption and treatment effectiveness. Further, the sulfapyridine is responsible for a majority of adverse effects of traditional sulfasalazine administration. The combination of sulfasalazine with gold decorated boron nitride particles has been suggested. However, such particles have the significant drawbacks of being expensive to produce, having a limited pharmacological effect, and not being well tolerated in the human body.

Thus, a composition for treating ulcerative colitis solving the aforementioned problems is desired.

SUMMARY

A composition for treating ulcerative colitis can include zinc oxide nanoparticles having sulfasalazine adsorbed on a surface thereon. The composition can be administered to a patient to treat ulcerative colitis or symptoms associated with ulcerative colitis. The composition can be administered to a patient in an amount of about 100 mg/kg zinc oxide nanoparticles, with about 12.2 mg/kg of sulfasalazine adsorbed thereon.

Another embodiment of the present subject matter relates to a method for treating ulcerative colitis in a subject comprising administering a therapeutically effective amount of a composition to a subject in need thereof, the composition comprising: zinc oxide nanoparticles; and sulfasalazine adsorbed onto a surface of the zinc oxide nanoparticles.

These and other features will become readily apparent upon further review of the following specification.

DETAILED DESCRIPTION OF THE PREFERRED EMBODIMENTS

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

A "subject" herein is typically a human. In certain embodiments, a subject is a non-human mammal. Exemplary non-human mammals include laboratory, domestic, pet, sport, and stock animals, e.g., mice, cats, dogs, horses, and cows. Typically, the subject is eligible for treatment, e.g., treatment of a gastrointestinal inflammatory disorder such as ulcerative colitis.

As used herein, the term "patient" refers to any single subject for which treatment is desired. In certain embodiments, the patient herein is a human. A subject can be considered to be in need of treatment.

As used herein, "gastrointestinal inflammatory disorders" or "bowel diseases, disorders, or conditions" are a group of chronic disorders that cause inflammation and/or ulceration in the mucous membrane. These disorders include, for example, inflammatory bowel disease (e.g., Crohn's disease, ulcerative colitis, indeterminate colitis and infectious colitis), mucositis (e.g., oral mucositis, gastrointestinal mucositis, nasal mucositis and proctitis), necrotizing enterocolitis and esophagitis. Inflammatory Bowel Disease (IBD) is used interchangeably herein to refer to diseases of the bowel that cause inflammation and/or ulceration and includes without limitation Crohn's disease and ulcerative colitis. Crohn's disease (CD) and ulcerative colitis (IX) are chronic inflammatory bowel diseases of unknown etiology. Crohn's disease, unlike ulcerative colitis, can affect any part of the bowel. The most prominent feature of Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Crohn's disease may involve any part of the alimentary tract from the mouth to the anus, although typically it appears in the ileocolic, small-intestinal or colonic-anorectal regions. Histopathologically, the disease manifests by discontinuous granulomatomas, crypt abscesses, fissures and aphthous ulcers. The inflammatory infiltrate is mixed, consisting of lymphocytes (both T and B cells), plasma cells, macrophages, and neutrophils. There is a disproportionate increase in IgM- and IgG-secreting plasma cells, macrophages and neutrophils.

Ulcerative colitis (UC) afflicts the large intestine. The course of the disease may be continuous or relapsing, mild or severe. The earliest lesion is an inflammatory infiltration with abscess formation at the base of the crypts of Lieberkuhm. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus, and mucus with scanty fecal particles. A total colectomy may be required for acute, severe or chronic, unremitting ulcerative colitis. The clinical features of UC are highly variable, and the onset may be insidious or abrupt, and may include diarrhea, tenesmus and relapsing rectal bleeding. With fulminant involvement of the entire colon, toxic megacolon, a life-threatening emergency, may occur. Extraintestinal manifestations include arthritis, pyoderma gangrenoum, uveitis, and erythema nodosum.

An "effective amount" of a composition as described herein is an amount sufficient to carry out a specifically stated purpose. An "effective amount" may be determined empirically and in a routine manner, in relation to the stated purpose. The term "therapeutically effective amount" refers to an amount of a composition as described herein to "treat" a disease or disorder in a subject.

As used herein, "suppressing", "suppress", or "suppression" means stopping the inflammation from occurring-, worsening, persisting, lasting, or recurring.

"Reducing", "reduce", or "reduction" means decreasing the severity, frequency, or length of one or more symptoms of a disease, disorder, or condition as described herein.

"Treating" or "treatment" or "alleviation" refers to both therapeutic treatment and prophylactic or preventative measures, wherein the object is to prevent or slow down (lessen) the targeted pathologic disease, condition, or disorder. Those in need of treatment include those already with the disease, condition, or disorder as well as those prone to have the disease, condition, or disorder or those in whom the disease, condition, or disorder is to be prevented. A subject or mammal is successfully "treated" for a disease, condition, or disorder if, after receiving a therapeutic amount of a composition as described herein, the subject shows observable and/or measurable reduction in, or absence of, one or more symptoms of the disease, condition, or disorder. Reduction of these signs or symptoms may also be felt by the patient.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In one embodiment, the present subject matter relates to a composition for treating ulcerative colitis comprising: zinc oxide nanoparticles; and sulfasalazine adsorbed onto a surface of the zinc oxide nanoparticles (ZnONPs). In certain embodiments, each 100 mg of zinc oxide nanoparticles can adsorb 12.2 mg of sulfasalazine.

In another embodiment, the present subject matter is directed to pharmaceutical compositions comprising a therapeutically effective amount of the composition as described herein together with one or more pharmaceutically acceptable carriers, excipients, or vehicles.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art.

The present compositions can be in any suitable unit dosage form such as tablets, pills, capsules, powders, or granules, for oral administration. In an embodiment, the pharmaceutical composition is in capsule form. In an embodiment, the capsule shell is starch-based.

The present composition can be typically administered at a therapeutically or pharmaceutically effective dosage, e.g., a dosage sufficient to provide treatment for ulcerative colitis or symptoms associated with ulcerative colitis. Administration of the pharmaceutical composition can be by any method that delivers the composition systemically and/or locally. These methods include oral routes, parenteral routes, intraduodenal routes, and the like.

A therapeutically effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

A method for treating ulcerative colitis can include administering a therapeutically effective amount of the composition to a subject in need thereof. The composition can include about 100 mg/kg of zinc oxide nanoparticles having about 12.2 mg/kg of sulfasalazine adsorbed thereon.

Each of sulfasalazine and zinc oxide has demonstrated certain effects on ulcerative colitis in a mammalian host system when administered alone. As described herein, however, profound synergistic effects can be achieved by administering sulfasalazine and zinc oxide nanoparticles as a single, fixed combination, with the sulfasalazine adsorbed on the surface of the zinc oxide nanoparticles, as a consortium to control the ulcerative colitis. The adsorption of the sulfasalazine on the surface of the zinc oxide nanoparticles can decrease the dose of sulfasalazine used to achieve an overall positive effect, as a result of the synergistic effect between the zinc oxide nanoparticles and the sulfasalazine.

In this regard, the combination of sulfasalazine: and the zinc oxide nanoparticles in the same formulation can limit and restrict the absorption of mesalazine (5-ASA), thereby avoiding hematological adverse effects. Further, because of the structure of the combination formulation, the therapeutic effect of the formulation can be based on a direct contact effect occurring between the formulation and an ulcerated colon.

In addition, the zinc oxide nanoparticles can act not only as a carrier for the sulfasalazine, but also as a physical binder of the sulfasalazine, and as a healing and antibacterial agent to potentiate the effect of the sulfasalazine in treating the ulcerative colitis, resulting in a powerful formulation for effectively treating ulcerative colitis. Similarly, the sulfasalazine can be an effective treatment for the ulcerative colitis due to its strong anti-inflammatory and immunomodulatory properties. This is particularly true in the instant compositions, which can provide a high concentration of intact sulfasalazine to the injured colon, without exhibiting any of the side effects of other known ulcerative colitis treatments such as, for example, sulfapyridine. That is, the zinc oxide nanoparticles permit a high concentration of intact sulfasalazine molecules to reach and treat an injured colon in the subject.

In certain embodiments, in the methods of treating ulcerative colitis herein, administration of the present composition can increase healing of ulcerative tissue and decreases inflammation in the ulcerative tissue in the patient or subject. In this regard, administration of the present composition can decrease colonic tissue tumor necrosis factor-α (TNF-α) interleukin 1beta (IL 1B), malondialdehyde (MDA), caspase-1, and cyclooxygenase-2 (COX2) in the subject.

In an embodiment, the present compositions can decrease the metabolic conversion of the sulfasalazine into 5-amino salicylic acid (5-ASA) and sulfapyridine, due to the adsorption of the sulfasalazine on the zinc oxide nanoparticles.

The present teachings are illustrated by the following examples.

Example 1

Forty male albino rats were randomly divided into four groups (n=10 rats), with all groups were treated for 7 days, as follows:

Group 1: Rats received saline daily for 21 consecutive days by rectal catheter and served as the normal control group (negative control).

Group 2: The disease group received 1 ml acetic acid 3% for three days and served as the ulcerative colitis (UC) control group (positive control).

Group 3: In the standard group, rats received free sulfasalazine (100 mg/kg; P.O. i.e., about 20 mg/rat 200 g) after induction of UC by acetic acid 3% as in group 2.

Group 4: The treatment group, where UC rats received the dose of ZnONPs loaded sulfasalazine (100 mg/kg; P.O. of the ZnONPs) containing: 12.2 mg sulfasalazine/kg; P.O.

Markers estimated:

Macroscopic examination of colonic mucosa.

Inflammatory mediators such as tumor necrosis factor-α (TNF-α), interleukin 1beta (IL 1B), malondialdehyde (MBA), reduced glutathione (GSH), superoxide dismutase (SOD), caspase-1, and cyclooxygenase-2 (COX2).

Inflammatory mediators are estimated by ELIZA.

ZnONPs, when administered alone, decreased the inflammatory mediator's colonic tissue factor, IL, TNF alpha, caspase-1, and MDA while increasing GSH, SOD, and antioxidant enzymes. But its effect was less than that seen for Group 4, the treatment group (sulfasalazine loaded ZnONPs). Similarly, the effect observed on Group 3, the standard group (sulfasalazine taken alone) was lower than that observed for Group 4.

In contrast, the present compositions administered as Group 4 significantly decreased the colonic tissue tumor necrosis factor-α (TNF-α), interleukin 1beta. (IL 1B), malondialdehyde (MDA), caspase-1, and cyclooxygenase-2 (COX2), and significantly reduced glutathione (GSH) and superoxide dismutase (SOD) when compared to standard sulfasalazine. This demonstrates the present compositions are better in increasing the healing of ulcerative tissues and decreasing inflammation, even though the formula contains a small dose of sulfasalazine when compared to the large dose of free sulfasalazine given in Group 3. Accordingly, the combination of sulfasalazine and the ZnONPS is more curative than each agent when taken alone (synergistic effect). This is attributed to the increased penetrative power of sulfasalazine by the aid of the ZnO nanoparticles.

Further, the mortality rate was zero % in Group 4 (treatment group) while it was 2% in Group 3 (standard group).

It is to be understood that the composition for treating ulcerative colitis is not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A composition for treating ulcerative colitis comprising:
    zinc oxide nanoparticles; and sulfasalazine adsorbed onto a surface of the zinc oxide nanoparticles.

2. The composition for treating ulcerative colitis as recited in claim 1, wherein each 100 fig of zinc oxide nanoparticles can adsorb 12.2 mg of sulfasalazine.

3. A method for treating ulcerative colitis in a subject comprising administering a therapeutically effective amount of a composition to a subject in need thereof, the composition comprising:
zinc oxide nanoparticles; and
sulfasalazine adsorbed onto a surface of the zinc oxide nanoparticles.

4. The method for treating ulcerative colitis as recited in claim 3, wherein about 100 mg/kg of the zinc oxide nanoparticles are administered to the subject.

5. The method for treating ulcerative colitis as recited in claim 4, wherein about 12.2 mg of the sulfasalazine are adsorbed onto the about 100 mg/kg of the zinc oxide nanoparticles.

6. The method for treating ulcerative colitis as recited in claim 3, wherein the zinc oxide nanoparticles and the sulfasalazine exhibit a synergistic effect in treating the ulcerative colitis.

7. The method for treating ulcerative colitis as recited in claim 3, wherein administration of the composition increases healing of ulcerative tissue and decreases inflammation in the ulcerative tissue.

8. The method for treating ulcerative colitis as recited in claim 3, wherein administration of the composition decreases colonic tissue tumor necrosis factor-$\alpha$ (TNF-$\alpha$), interleukin 1beta (IL 1B), malondialdehyde (MDA), caspase-1, and cyclooxygenase-2 (COX2) in the subject.

9. The method for treating ulcerative colitis of claim 6, wherein the zinc oxide nanoparticles increase penetrative power of the sulfasalazine, resulting in the synergistic effect.

10. The method for treating ulcerative colitis as recited in claim 6, wherein the zinc oxide nanoparticles potentiate the effect of the sulfasalazine in treating the ulcerative colitis.

11. The method for treating ulcerative colitis as recited in claim 3, wherein the zinc oxide nanoparticles permit a high concentration of intact sulfasalazine molecules to reach and treat an injured colon in the subject.

\* \* \* \* \*

UNITED STATES PATENT AND TRADEMARK OFFICE
CERTIFICATE OF CORRECTION

| | |
|---|---|
| PATENT NO. | : 11,730,759 B1 |
| APPLICATION NO. | : 18/119526 |
| DATED | : August 22, 2023 |
| INVENTOR(S) | : Hany Mohamed Abd El-Lateef Ahmed et al. |

It is certified that error appears in the above-identified patent and that said Letters Patent is hereby corrected as shown below:

On the Title Page

Inventors Item (72), for Inventors 3-5, please delete and replace with the updated residences as follows:
AHMED MOHAMMED ABU-DIEF MOHAMMED, Al-Madina Al-Mounawara, SAUDI ARABIA; MOHAMMED SHERIF SADDIK IBRAHIM, Sohag, EGYPT; ALI KHAMES ABD ELTWAB MORSY, Sohag, EGYPT.

Signed and Sealed this
Twenty-eighth Day of May, 2024

Katherine Kelly Vidal
*Director of the United States Patent and Trademark Office*